(12) United States Patent  
Vo et al.

(10) Patent No.: US 11,332,657 B2
(45) Date of Patent: May 17, 2022

(54) DUAL CATION HYDRATE INHIBITORS

(71) Applicant: Multi-Chem Group, LLC, Houston, TX (US)

(72) Inventors: Loan Vo, Houston, TX (US); Deepak S. Monteiro, Houston, TX (US); Qiang Lan, The Woodlands, TX (US); Philippe Prince, Pearland, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 21 days.

(21) Appl. No.: 16/753,213

(22) PCT Filed: May 23, 2019

(86) PCT No.: PCT/US2019/033656
§ 371 (c)(1),
(2) Date: Apr. 2, 2020

(87) PCT Pub. No.: WO2020/236176
PCT Pub. Date: Nov. 26, 2020

(65) Prior Publication Data
US 2021/0071065 A1    Mar. 11, 2021

(51) Int. Cl.
*C09K 8/52* (2006.01)
*C07C 237/06* (2006.01)
*E21B 43/00* (2006.01)

(52) U.S. Cl.
CPC .............. *C09K 8/52* (2013.01); *C07C 237/06* (2013.01); *E21B 43/00* (2013.01); *C09K 2208/22* (2013.01)

(58) Field of Classification Search
CPC ... C07C 237/00; C07C 237/02; C07C 237/04; C07C 237/06; C07C 237/08;
(Continued)

(56) References Cited

U.S. PATENT DOCUMENTS 10,011,756 B2    7/2018  Lan
10,100,241 B2 *  10/2018 Lan ........................ C09K 8/524
(Continued)

FOREIGN PATENT DOCUMENTS

JP    2001048851 A  * 2/2001
WO    2017/105507 A1   6/2017
WO    2017/184113 A1   10/2017

OTHER PUBLICATIONS

International Search Report and Written Opinion issued in related PCT Application No. PCT/US2019/033656 dated Feb. 19, 2020, 10 pages.
(Continued)

*Primary Examiner* — Angela M DiTrani Leff
(74) *Attorney, Agent, or Firm* — Tenley Krueger; Baker Botts L.L.P.

(57) ABSTRACT

Dual cation hydrate inhibitor compositions and methods of using such compositions to, for example, inhibit the formation of gas hydrate agglomerates are provided. In some embodiments, such methods include introducing a hydrate inhibitor composition into a fluid, wherein the hydrate inhibitor composition includes at least one compound having the structural formula:

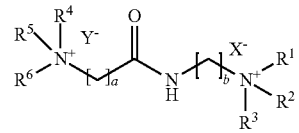

wherein each of $R^1$, $R^2$, and $R^3$ is independently a $C_1$ to $C_6$ hydrocarbon chain, wherein $R^4$ is selected from the group consisting of hydrogen and any $C_1$ to $C_{50}$ hydrocarbon chain, wherein each of $R^5$ and $R^6$ is independently selected from the group consisting of hydrogen and a $C_1$ to $C_{50}$ hydrocarbon chain, wherein $X^-$ and $Y^-$ are counter anions, and wherein each of a and b is independently an integer from 1 to 10.

20 Claims, 3 Drawing Sheets

(58) Field of Classification Search
CPC ....... C07C 237/10; C07C 237/12; C09K 8/52; C09K 8/524; C09K 8/528; C09K 2208/02
See application file for complete search history.

(56) References Cited

U.S. PATENT DOCUMENTS

| | | | |
|---|---|---|---|
| 2004/0163306 A1* | 8/2004 | Dahlmann | C07C 7/20 44/405 |
| 2005/0081432 A1* | 4/2005 | Panchalingam | C10L 3/003 44/419 |
| 2005/0261529 A1* | 11/2005 | Crosby | C07C 7/20 585/15 |
| 2006/0237691 A1 | 10/2006 | Meier et al. | |
| 2012/0161070 A1* | 6/2012 | Webber | C10L 3/107 252/182.29 |
| 2016/0102240 A1 | 4/2016 | Zhao et al. | |
| 2016/0122619 A1 | 5/2016 | Lucente-Schultz et al. | |

OTHER PUBLICATIONS

International Preliminary Report on Patentability issued in related PCT Application No. PCT/US2019/033656 dated Dec. 2, 2021, 7 pages.

* cited by examiner

DUAL CATION HYDRATE INHIBITORS

BACKGROUND

The present disclosure relates to compositions and methods useful in processes involving fluid flowing through, or contained in, wellbores penetrating subterranean formations, vessels, or conduits, such as pipes used, e.g., for the production and/or transport of petroleum products, natural gas, and the like.

Gas hydrates are solids that may agglomerate in a fluid that is flowing or is substantially stationary, under certain temperature and pressure conditions. For example, gas hydrates may form during hydrocarbon production from a subterranean formation, in particular in pipelines and other equipment during production operations. Hydrates may impede or completely block flow of hydrocarbons or other fluid flowing through such pipelines. These blockages not only may decrease or stop production, potentially costing millions of dollars in lost production, but also may be very difficult and dangerous to mediate. Unless properly handled, gas hydrates may be volatile and/or explosive, potentially rupturing pipelines, damaging equipment, endangering workers, and/or causing environmental harm.

Gas hydrates may form when water molecules become bonded together after coming into contact with certain "guest" gas or liquid molecules. Hydrogen bonding causes the water molecules to form a regular lattice structure, like a cage, that is stabilized by the guest gas or liquid molecules entrapped within the lattice structure. The resulting crystalline structure may precipitate as a solid gas hydrate. Guest molecules can include any number of molecules such as, for example, carbon dioxide, methane, butane, propane, hydrogen, helium, freon, halogen, noble gases, and the like.

BRIEF DESCRIPTION OF THE DRAWINGS

These drawings illustrate certain aspects of some of the embodiments of the present disclosure and should not be used to limit or define the claims.

Figure 1:
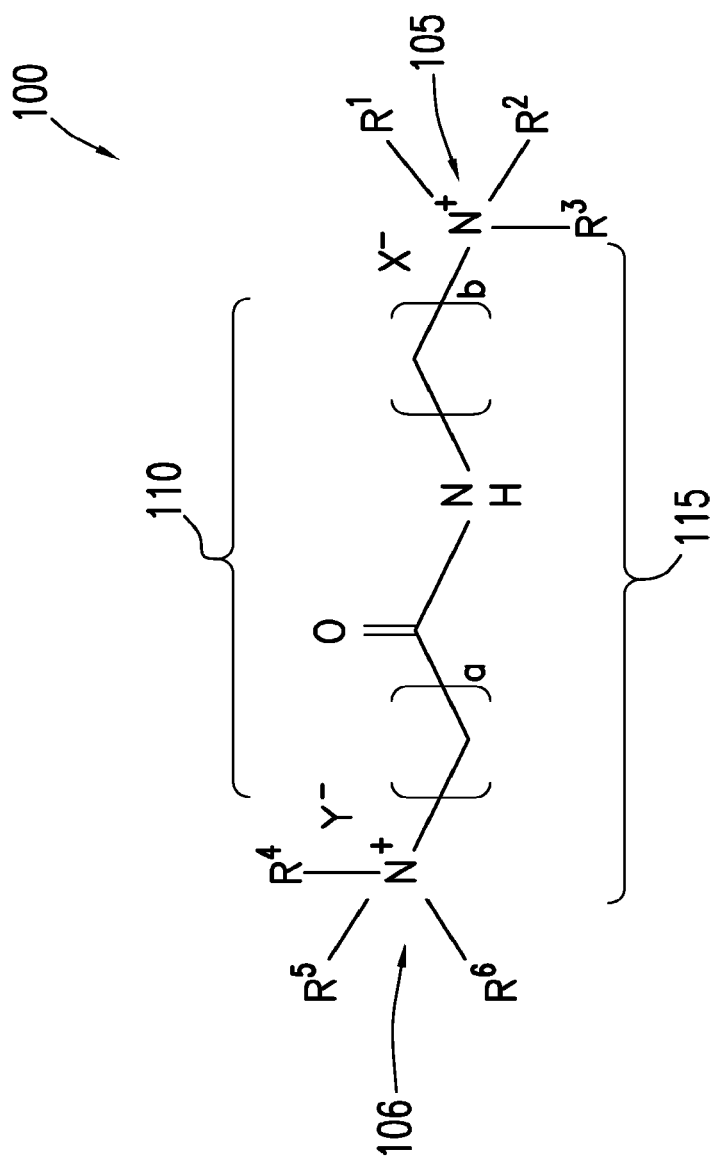
FIG. 1 is a diagram illustrating a hydrate inhibitor compound in accordance with certain embodiments of the present disclosure.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure involving wellbores may be applicable to horizontal, vertical, deviated, or otherwise nonlinear wellbores in any type of subterranean formation. Embodiments may be applicable to injection wells, monitoring wells, and production wells, including hydrocarbon or geothermal wells.

The present disclosure relates to compositions and methods useful in processes involving fluid flowing through, or contained in, wellbores penetrating subterranean formations or conduits, such as pipes used, e.g., for the production and/or transport of petroleum products, natural gas, and the like. More particularly, the present disclosure relates to compositions and method of using such compositions to, for example, inhibit the formation of gas hydrate agglomerates.

In certain embodiments, the present disclosure may provide hydrate inhibitor compounds (e.g., LDHIs) including one or more lipophilic tails, one or more hydrophilic heads, and a linking moiety. In some embodiments, the hydrate inhibitor compounds may be provided, used, and/or introduced as a salt. In certain embodiments, the present disclosure further provides methods of using such hydrate inhibitor compounds to inhibit the formation of one or more hydrates in a fluid. For example, certain embodiments of the present disclosure provide methods of adding a composition including one or more hydrate inhibitor compounds of the present disclosure to a fluid which may include any one or more of water, a gas, a liquid hydrocarbon, and any combination thereof. In certain embodiments, such a method may include adding to the fluid an effective amount of a hydrate inhibitor compound of the present disclosure to inhibit, retard, reduce, control, delay, and/or the like the formation of hydrate agglomerates.

Among the many advantages to the compositions and methods of the present disclosure, only some of which are alluded to herein, the hydrate inhibitor compounds and methods of the present disclosure may, among other benefits, provide for enhanced anti-agglomeration properties and/or enhanced inhibition, retardation, mitigation, reduction, control, delay, and/or the like of agglomeration of hydrates and/or hydrate-forming compounds. In certain embodiments, agglomeration of hydrates and/or hydrate-forming compounds (and the like) may be reduced and/or inhibited to a greater degree than that achieved using other hydrate inhibition means. In particular embodiments, compounds of the present disclosure may provide enhanced inhibition of agglomeration of hydrates and/or hydrate-forming compounds.

The hydrate inhibitor compounds of the present disclosure may include two or more cation moieties. In some embodiments, the hydrate inhibitor compound may include a first cation moiety including a first quaternary ammonium cation moiety. In certain embodiments, the first cation moiety may include a hydrophilic head. In certain embodiments, the hydrate inhibitor compound includes a second cation moiety including a tertiary ammonium cation or a quaternary ammonium cation. FIG. 1 illustrates the chemical structure for certain hydrate inhibitor compounds of the present disclosure. In certain embodiments, the cation moieties in the hydrate inhibitor compounds of the present disclosure may be bonded to other moieties of the hydrate inhibitor compound, for example, as shown with respect to the cation moieties 105 and 106 of the hydrate inhibitor compound 100 in FIG. 1. In certain embodiments, the cation moieties may be substantially of the composition —$R^1R^2R^3N^+$— and —$R^4R^5R^6N^+$—. Each of $R^1$, $R^2$, and $R^3$ may independently include a $C_1$ to $C_6$ hydrocarbon chain. With further reference to FIG. 1, $R^4$ may include a hydrogen atom or a $C_1$ to $C_{50}$ hydrocarbon chain, $R^5$ may include a $C_1$ to $C_{50}$ hydrocarbon chain, and $R^6$ may include a $C_1$ to $C_{50}$ hydrocarbon chain. In certain embodiments, $R^6$ may include a $C_1$ to $C_6$ hydrocarbon chain.

As used herein, a "hydrocarbon chain" may, unless otherwise specifically noted, be branched, unbranched, non-cyclic, and/or cyclic; it may be substituted or unsubstituted (that is, it may or may not contain one or more additional moieties or functional groups in place of one or more hydrogen atoms in the hydrocarbon chain); and/or it may be saturated or unsaturated. Furthermore, as used herein, the nomenclature "$C_x$ to $C_y$" refers to the number of carbon atoms in the hydrocarbon chain (here, ranging from x to y carbon atoms). As used herein, "independently" refers to the notion that the preceding items may be the same or different.

In certain embodiments, $R^1$, $R^2$, and/or $R^3$ may independently include a $C_1$ to $C_6$ alkyl chain. In such embodiments wherein at least one of $R^1$, $R^2$, and/or $R^3$ includes a $C_1$ to $C_6$ hydrocarbon chain, the hydrocarbon chain may include any one or more hydrocarbon groups selected from the group consisting of: alkyl, alkenyl, alkynyl, aryl, arylalkyl, arylalkenyl, alkylaryl, alkenylaryl, and any combination thereof. In such embodiments, any one or more of $R^1$, $R^2$, and $R^3$ may be branched, unbranched, non-cyclic, cyclic, saturated, and/or unsaturated. In certain embodiments, each of $R^1$, $R^2$, and $R^3$ may independently include (i) as few as any one of: 1, 2, 3, 4, 5, and 6 carbon atoms, and (ii) as many as one of: 2, 3, 4, 5, and 6 carbon atoms. For example, suitable ranges of numbers of carbon atoms in each of $R^1$, $R^2$, and $R^3$ according to various embodiments of the present disclosure include, but are not limited to, 1 to 2, 1 to 3, 1 to 4, 1 to 5, 1 to 6, 2 to 4, 3 to 5, and 4 to 6, and the like.

In some embodiments, any one or more of $R^1$, $R^2$, and $R^3$ may include a $C_1$ to $C_6$ alkyl chain. In some embodiments, any one or more of $R^1$, $R^2$, and $R^3$ may include a $C_2$ to $C_6$ alkenyl or alkynyl chain (in which case at least 2 carbon atoms are necessary to form an alkenyl or alkynyl chain). In some embodiments, any one or more of $R^1$, $R^2$, and $R^3$ may include a $C_3$ to $C_6$ cyclic moiety (in which case at least 3 carbon atoms are necessary to form a cyclic moiety). In certain embodiments, any one or more of $R^1$, $R^2$, and $R^3$ may be substituted (e.g., may include any one or more functional groups in addition to the hydrocarbon groups described above), so long as the cation moiety remains hydrophilic.

In some embodiments, $R^5$ and $R^6$ may independently include a $C_1$ to $C_{50}$ hydrocarbon chain. In certain embodiments, $R^4$ may be a hydrogen atom. In those embodiments, the cation moiety —$R^4R^5R^6N^+$— is a tertiary ammonium cation moiety. In other embodiments, $R^4$ is not a hydrogen atom. In those embodiments, each of $R^4$, $R^5$, and $R^6$ may independently include a $C_1$ to $C_{50}$ hydrocarbon chain, and the cation moiety —$R^4R^5R^6N^+$— may be a quaternary ammonium cation moiety. In such embodiments wherein at least one of $R^4$, $R^5$, and $R^6$ include a $C_1$ to $C_{50}$ hydrocarbon chain, the hydrocarbon chain may include any one or more hydrocarbon groups selected from the group consisting of: alkyl, alkenyl, alkynyl, aryl, arylalkyl, arylalkenyl, alkylaryl, alkenylaryl, and any combination thereof. In such embodiments, any one or more of $R^4$, $R^5$, and $R^6$ may be branched, unbranched, non-cyclic, cyclic, saturated, and/or unsaturated. In certain embodiments, each of $R^4$, $R^5$, and $R^6$ may independently include (i) as few as any one of: 1, 2, 3, 4, 5, 6, 7, 8, 9, 10, 11, 12, 13, 14, 15, 16, 17, 18, 19, and 20 carbon atoms, and (ii) as many as one of: 35, 36, 37, 38, 39, 40, 41, 42, 43, 44, 45, 46, 47, 48, 49, and 50 carbon atoms. For example, suitable ranges of numbers of carbon atoms in each of $R^4$, $R^5$, and $R^6$ according to various embodiments of the present disclosure include, but are not limited to, 1 to 50, 1 to 40, 1 to 30, 1 to 20, 1 to 10, 1 to 6, 2 to 10, and 5 to 10, and the like.

In some embodiments, any one or more of $R^4$, $R^5$, and $R^6$ may include a $C_1$ to $C_{50}$ alkyl chain. In certain embodiments, any one or more of $R^4$, $R^5$, and $R^6$ may be substituted (e.g., may include any one or more functional groups in addition to the hydrocarbon groups described above).

The hydrate inhibitor compounds of the present disclosure may further include one or more lipophilic tails. For example, with reference to FIG. 1, $R^4$, $R^5$, and/or $R^6$ of the hydrate inhibitor compound 100 may include a lipophilic tail. In some embodiments, only one of $R^4$, $R^5$, and $R^6$ is a lipophilic tail. In certain embodiments, the hydrocarbon chain of the lipophilic tail(s) may be branched or unbranched, cyclic or non-cyclic, saturated or saturated, and/or may be any one or more of alkyl, alkenyl, alkynyl, and aryl groups, and/or any combination thereof. In certain embodiments, the lipophilic tail(s) may further optionally be substituted with any one or more functional groups, so long as such substituted functional group(s) do not alter the lipophilic and/or hydrophobic nature of the lipophilic tail(s). In certain embodiments, each of the lipophilic tails may independently include (i) as few as any one of: 1, 2, 3, 4, 5, 6, 7, 8, 9, 10, 11, 12, 13, 14, 15, 16, 17, 18, 19, and 20 carbon atoms, and (ii) as many as any one of: 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, and 50 carbon atoms. For example, suitable ranges of numbers of carbon atoms in the lipophilic tail(s) according to various embodiments of the present disclosure include, but are not limited to 1 to 5, 3 to 5, 4 to 8, 5 to 15, 8 to 18, 12 to 16, 8 to 20, 10 to 20, 15 to 20, and the like. It will be appreciated by one of ordinary skill in the art having the benefit of the present disclosure that even in such embodiments, additional lipophilic tails could be included in the hydrate inhibitor compound (e.g., at a point along the backbone 115 of the hydrate inhibitor compound 100).

The hydrate inhibitor compounds of the present disclosure may further include a linking moiety. As used herein, "linking moiety" refers to any portion of the hydrate inhibitor compound that provides spacing between the cation moieties and/or the lipophilic tail(s). In certain embodiments, one or more lipophilic tails may be connected to the cation moieties via the linking moiety. In some embodiments, two or more cation moieties may be connected to the each other via a linking moiety. For example, in the hydrate inhibitor compound 100 shown in FIG. 1, first cation moiety 105 is connected to second cation moiety 106 via linking moiety 110.

In certain embodiments, the linking moiety may each include one or more hydrocarbon chains of any length, branched or unbranched, and/or saturated or unsaturated (so long as the overall hydrate inhibitor compound maintains amphiphilic character). Hydrocarbon chain lengths include $C_1$ to $C_{50}$ chains or longer. In certain embodiments, the linking moiety may be any one or more of methyl, ethyl, propyl, butyl, pentyl, hexyl, heptyl, octyl, nonyl, decyl, etc. In certain embodiments, the linking moiety may be substituted such that it includes any kind and any number of functional groups (so long as the hydrate inhibitor compound maintains both hydrophobic and hydrophilic portions). In such embodiments, the one or more functional groups that may be included on the linking moiety according to some embodiments should not adversely affect the hydrophilic nature of a hydrophilic head, nor should they adversely affect the lipophilic nature of the lipophilic tail(s). Examples of suitable functional groups that may be included in the linking moiety, the lipophilic tail(s), and/or the R-groups ($R^1$, $R_2$, $R^3$, $R^4$, $R^5$, $R^6$) of the present disclosure may include any one or more of: an ester, ether, amine, sulfonamide, amide, ketone, carbonyl, isocyanate, urea, urethane, and any combination thereof. In some embodiments, the one or more functional groups on the linking moiety may include any group capable of reacting with an amine, provided that functional group's inclusion in the linking moiety allows the hydrate inhibitor compound to maintain its amphiphilic character.

For example, the hydrate inhibitor compound 100 of FIG. 1 includes example linking moiety 110 including an amide group as well as two alkyl chains of the general formulas $C_aH_{2a}$ and $C_bH_{2b}$ on either side of the amide group. In certain embodiments, each of a and b may independently be an integer from 1 to 10. In certain embodiments, each alkyl chain in the linking moiety may include (i) as few as any one of: 1, 2, 3, 4, 5, 6, 7, 8, 9, and 10 carbon atoms, and (ii) as many as any one of: 2, 3, 4, 5, 6, 7, 8, 9, and 10 carbon atoms.

The hydrate inhibitor compounds of the present disclosure may instead or in addition be characterized as reaction products. For instance, in some embodiments, the present disclosure provides hydrate inhibitor compounds that may be characterized as reaction products of: (1) a dialkylaminoalkylamine having the general formula $H_2N-(CH_2)_c-NR^1R^2$ and (2) a first intermediate formed as the reaction product of one or more unsaturated carboxylic acids or esters containing an alkene chain (e.g., acrylates) and an amine. In some embodiments, the "dialkyl" groups of the dialkylaminoalkylamine may be either the same or different, and the $R^1$ and $R^2$ groups may depend upon, among other factors, the identity of the dialkyl groups of the dialkylaminoalkylamine. In certain embodiments, the length of the "alkyl" chain (i.e., $(CH_2)_c$) of the dialkylaminoalkylamine may vary from $(CH_2)_1$ to $(CH_2)_{10}$, and the length of an alkyl chain in the linking moiety having the general formula $C_bH_{2b}$ may depend upon, among other factors, the length of the alkyl chain of the dialkylaminoalkylamine. In certain embodiments, the unsaturated carboxylic acids or esters containing an alkene chain may be an alkyl alkenoate (e.g., an alkyl methacrylate, an alkyl acrylate (for example, methyl acrylate)), an alkenoic acid (e.g., acrylic acid), and any combination thereof. In certain embodiments, the length of an alkyl chain in the linking moiety having the general formula $C_aH_{2a}$ may depend upon, among other factors, the identity of the unsaturated carboxylic acid or ester.

In certain embodiments, the amine may have one or more hydrocarbon chains each of a length from $C_1$ to $C_{50}$, and the lipophilic tails $R^4$ and $R^5$ of the hydrate inhibitor compound may depend upon, among other factors, the identity of the hydrocarbon chains. In certain embodiments, the amine may include one or more functional groups and a portion of the functional group may be included in the lipophilic tails $R^4$ and $R^5$ of the hydrate inhibitor compound. In some embodiments, $R^4$ and $R^5$ include $C_1$ to $C_{50}$ hydrocarbon chains resulting from a reaction between an acrylate or a methacrylate and an amine. Suitable amines for reaction may include, but are not limited to, any primary or secondary fatty amine derived from one or more fatty acids selected from the group consisting of: corn oil, canola oil, coconut oil, safflower oil, sesame oil, palm oil, cottonseed oil, soybean oil, olive oil, sunflower oil, hemp oil, wheat germ oil, palm kernel oil, vegetable oil, tall oil, tallow oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof. Suitable amines for reaction also may include, but are not limited to, any synthetic primary or secondary amine including, but not limited to, butylamine, pentylamine, hexylamine, octylamine, dodecylamine, N-methyldodecylamine, N-methyloctylamine, didodecylamine, and the like, and any combination thereof.

In some embodiments, the reaction product of (1) the dialkylaminoalkylamine and (2) the first intermediate may form a second intermediate that may further be reacted with (3) one or more alkylating agents. In such embodiments, $R^3$ and/or $R^6$ of the cation moieties may depend upon, among other factors, the alkyl group of the alkylating agent(s). In certain embodiments, the one or more alkylating agents may be a carbonate, a halide, a sulfate, an organic sulfonate, a phosphate, a phosphonate, a hydroxide, and/or any combination thereof. In some embodiments, the alkylating agent may include a diethyl sulfate. In certain embodiments, the hydrate inhibitor compound is a reaction product of a reaction between (i) an alkylating agent and (ii) a second intermediate resulting from a reaction between a dialkylaminoalkylamine and a first intermediate, the first intermediate resulting from a reaction between an acrylate or a methacrylate and an amine.

Figure 2:
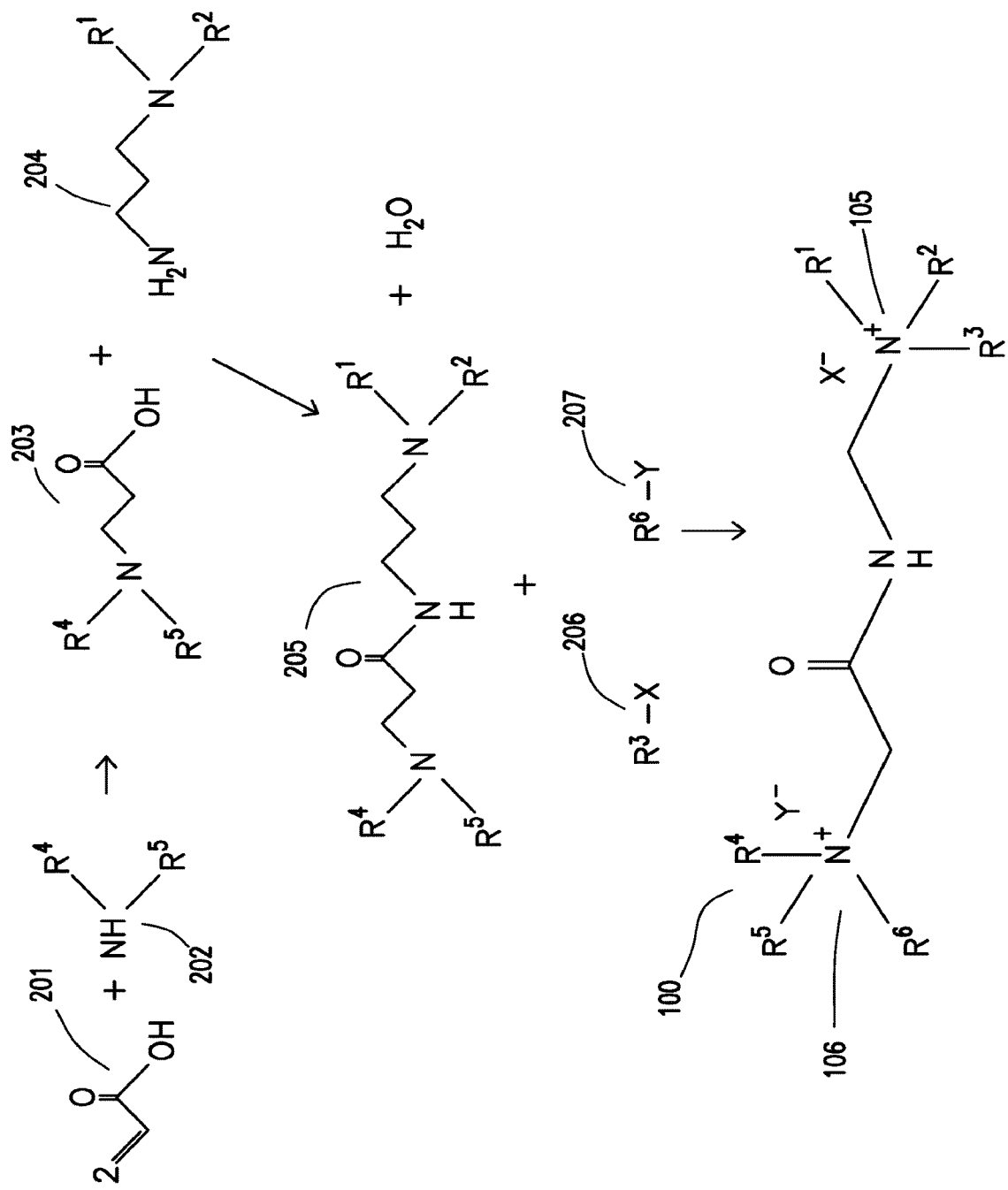
FIG. 2 is a diagram illustrating an example reaction process used to prepare a hydrate inhibitor compound in accordance with certain embodiments of the present disclosure.

FIG. 2 illustrates a potential reaction scheme for forming a hydrate inhibitor compound in accordance with certain embodiments of the present disclosure. In the reaction scheme shown, acrylic acid 201 reacts with amine 202 (which, as shown in FIG. 2, includes hydrocarbon chains $R^4$ and $R^5$) to produce first intermediate 203. The first intermediate 203 in turn reacts with dialkylaminopropylamine 204 (which, as shown in FIG. 2, includes hydrocarbon chains $R^1$ and $R^2$) forming a second intermediate 205. The second intermediate 205 in turn reacts with one or more alkylating agents 206 and 207 (which, as shown in FIG. 2, include hydrocarbon chains $R^3$ and $R^6$) to form hydrate inhibitor compound 100. As can be seen, hydrate inhibitor compound 100 includes two cation moieties 105 and 106 including R-groups $R^1$ and $R^2$ (retaining the hydrocarbon structure $R^1$ and $R^2$ of dialkylaminopropylamine 204), R-group $R^3$ (retaining the hydrocarbon structure $R^3$ of alkylating agent 206), $R^4$ and $R^5$ (retaining the hydrocarbon structures $R^4$ and $R^5$ of amine 202) and $R^6$ (retaining the hydrocarbon structure $R^6$ of alkylating agent 207) and a linking moiety including an amide group with an alkyl chain on each side of the amide group and an amino group connected to $R^4$ and $R^5$. The alkylating agents 206 and 207 may be the same or different. Such reactions may in some embodiments take place at about 80° C. to about 250° C. at approximately atmospheric pressure or lower pressure. It will be appreciated by one of ordinary skill in the art having the benefit of the present disclosure that various modifications may be made to this reaction scheme to produce other embodiments.

In certain embodiments, the hydrate inhibitor compounds of the present disclosure may be provided, used, and/or introduced as a salt of one or more of the compounds described herein. In such embodiments, the salt may include one or more counter anions. For example, the hydrate inhibitor compound 100 as shown in FIGS. 1 and 2 includes a salt with counter anions X⁻ and Y⁻. In certain embodiments, such salts may wholly or partially dissociate in aqueous solution. In other embodiments, the salts may remain substantially associated (either with the original anion or with other ions from solution). The suitable counter anions may include, for example, a carboxylate, a halide, a sulfate, an organic sulfonate, a hydroxide, and/or any combination thereof. It will be appreciated by one of ordinary skill in the art having the benefit of this disclosure that salts may be formed with other counter anions instead of or in addition to the counter anions specifically disclosed herein.

In certain embodiments, the hydrate inhibitor compounds of the present disclosure may have substantially the following structural formula:

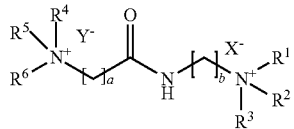

In such embodiments, each of $R^1$, $R^2$, and $R^3$ may independently include a $C_1$ to $C_6$ hydrocarbon chain; $R^4$ may include a hydrogen atom or a $C_1$ to $C_{50}$ hydrocarbon chain; $R^5$ and $R^6$ are each independently selected from the group consisting of hydrogen and a $C_1$ to $C_{50}$ hydrocarbon chain; X and Y may independently be counter anions according to the previous discussion; and each of a and b may be independently an integer from 1 to 10 according to the previous discussion of the alkyl chains of the linking moiety.

As previously noted, the present disclosure in some embodiments further provides methods of using the hydrate inhibitor compounds of the present disclosure. In certain embodiments, the hydrate inhibitor compounds of the present disclosure may be used to inhibit, retard, mitigate, reduce, control, and/or delay the formation of one or more hydrates or agglomerates of hydrates. For example, the hydrate inhibitor compounds of the present disclosure may be used to reduced and/or prevent hydrate particles from agglomerating by, for example, ensuring the hydrate particles remain small in size, well-dispersed in a fluid, and/or non-adherent to other hydrate particles and surfaces the hydrate particles may contact (e.g., conduit wall). Without limiting the present disclosure to a particular theory, it is believed that the hydrate inhibitor compounds of the present disclosure may attach to the surface of hydrate particles and that the lipophilic tail of the hydrate inhibitor compounds may reduce and/or prevent agglomeration and/or aggregation of the hydrate particles and/or may help to disperse the hydrate particles in a fluid.

In certain embodiments, one or more hydrate inhibitor compounds of the present disclosure may be introduced into a fluid including any one or more of water, a gas, a liquid hydrocarbon, and any combination thereof. Although listed separately from liquid hydrocarbon, the gas may in some embodiments include gaseous hydrocarbon, though the gas need not necessarily include hydrocarbon. In some embodiments, the gas may include, but is not limited to, $O_2$, $H_2$, $N_2$, $CO_2$, $CH_4$, $H_2S$, Ar, Kr, Xe, a hydrocarbon, a freon, and any combination thereof. In certain embodiments, the hydrate inhibitor compound may be introduced into the fluid through a conduit or an injection point. In certain embodiments, one or more hydrate inhibitor compounds of the present disclosure may be introduced into a wellhead, a wellbore, a subterranean formation, a conduit, a vessel, and the like and may contact and/or be introduced into a fluid residing therein.

In certain embodiments, the fluid may be flowing or it may be substantially stationary. In some instances, the fluid may be in a high-pressure, low-temperature environment such that hydrates form in the fluid. In certain embodiments, hydrates may form in the fluid when the pressure of the environment in which the fluid flows or resides is in the range from about 14.7 psi to about 20,000 psi. In certain embodiments, hydrates may form in the fluid when the temperature of the environment in which the fluid flows or resides is in the range from about 0° C. (32° F.) to about 30° C. (86° F.). In certain embodiments, the formation of hydrates in a fluid may depend on both the pressure and the temperature of the fluid and/or the environment in which the fluid is located. For example, at lower temperatures (e.g., below about 5° C. (41° F.)), methane hydrates may form over a wide range of pressures (e.g., above about 400 psi). Conversely, at higher pressures (e.g., above about 1400 psi), methane hydrates may form over a wide range of temperatures (e.g., up to about 15° C. (59° F.)).

In certain embodiments, the fluid may be within a vessel, or within a conduit (e.g., a conduit that may transport the fluid), or within a subterranean formation, or within a wellbore penetrating a portion of the subterranean formation, and/or within a wellhead of a wellbore. Examples of conduits include, but are not limited to, pipelines, production piping, subsea tubulars, process equipment, and the like as used in industrial settings and/or as used in the production of oil and/or gas from a subterranean formation, and the like. The conduit may in certain embodiments penetrate at least a portion of a subterranean formation, as in the case of an oil and/or gas well. In particular embodiments, the conduit may be a wellhead, a wellbore, or may be located within a wellbore penetrating at least a portion of a subterranean formation. Such oil and/or gas well may, for example, be a subsea well (e.g., with the subterranean formation being located below the sea floor), or it may be a surface well (e.g., with the subterranean formation being located belowground). A vessel or conduit according to other embodiments may be located in an industrial setting such as a refinery (e.g., separation vessels, dehydration units, pipelines, heat exchangers, and the like), or it may be a transportation pipeline.

In some embodiments, the hydrate inhibitor compounds of the present disclosure initially may be incorporated into a composition prior to being introduced into the fluid. The composition may be any suitable composition in which the hydrate inhibitor compound may be included. For example, in some embodiments, the composition may be a treatment fluid for use in a wellbore penetrating a subterranean formation during, for instance, oil and/or gas recovery operations. The composition may include a solvent for the hydrate inhibitor compound. Suitable solvents include, for example, any alcohol, methanol, ethanol, isopropyl alcohol, glycol, glycol ethers, any organic solvent, toluene, xylene, monobutyl ether, hexane, cyclohexane, and/or any combination thereof.

In certain embodiments, one or more hydrate inhibitor compounds of the present disclosure may be introduced into and/or contact the fluid in an amount from about 0.1% to about 10% by volume based on the volume of water in the fluid (or in other words, about 0.1% to about 10% by volume based on water cut). In various embodiments, the hydrate inhibitor compounds of the present disclosure may be used as low dosage hydrate inhibitors (LDHIs) such that an effective amount of one or more hydrate inhibitor compounds for inhibiting, retarding, mitigating, reducing, controlling, delaying, and/or the like agglomeration of hydrates may be as low as any of: 0.1, 0.25, 0.50, 0.75, 1.00, 1.25, 1.50, 1.75, 2.00, 2.25, and 2.50% by volume based on water cut. An effective amount may be as high as any of: 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, and 10.0% by volume based on water cut. Thus, in some embodiments, an effective amount of hydrate inhibitor compounds of the present disclosure for inhibiting, retarding, mitigating, reducing, controlling, delaying, and/or the like agglomeration of hydrates may be about 0.1% to about 5.5% by volume based on water cut of the fluid; in other embodiments, about 0.1% to about 3.0% by volume based on water cut of the fluid; in other embodiments, about 0.25% to about 2.5% by volume based on water cut of the fluid; and in other embodiments, about 0.5% to about 2.0% by volume based on water cut of the fluid.

In certain embodiments, one or more hydrate inhibitor compounds of the present disclosure may be introduced to and/or contact any of various fluids having different water cuts (i.e., the ratio of the volume of water in the fluid to the total volume of the fluid). For example, in some embodiments the water cut of the fluid may be about 1 to about 65%. In other embodiments, the water cut may be as low as any one of: 20, 25, 30, 35, 40, 45, 50, 55, 60, and 65%; while the water cut may be as high as any one of: 35, 40, 45, 50, 55, 60, 65, 70, 75, 80, 85, 90, and 95%. In certain embodiments, a fluid may have a water cut of 30% or more, 35% or more, 40% or more, 45% or more, 50% or more, 55% or more, or 60% or more, up to about 99%. In yet other embodiments, one or more hydrate inhibitor compounds of the present disclosure may be introduced into or contact a fluid with any water cut ranging from about 1% to about 99%.

In certain embodiments, the fluid to which one or more hydrate inhibitor compounds of the present disclosure may be introduced optionally may include any number of additives. Examples of such additives include, but are not limited to, salts, surfactants, acids, proppant particulates, diverting agents, fluid loss control additives, nitrogen, carbon dioxide, surface modifying agents, tackifying agents, foamers, corrosion inhibitors, scale inhibitors, other hydrate inhibitors, catalysts, clay control agents, biocides, friction reducers, antifoam agents, bridging agents, flocculants, $H_2S$ scavengers, $CO_2$ scavengers, oxygen scavengers, lubricants, viscosifiers, breakers, weighting agents, relative permeability modifiers, resins, wetting agents, coating enhancement agents, filter cake removal agents, antifreeze agents (e.g., glycols), and the like. A person skilled in the art, with the benefit of this disclosure, will recognize the types of additives that may be included in the fluids of the present disclosure for a particular application. It further will be appreciated by one of ordinary skill in the art having the benefit of the present disclosure that the amount of the hydrate inhibitor compounds of the present disclosure effective for inhibiting, retarding, reducing, controlling, delaying, and/or the like hydrates may depend upon, for example, the volume of water in the fluid and/or additives in the fluid.

In certain embodiments, the hydrate inhibitor compounds of the present disclosure may be introduced into a wellhead of a wellbore penetrating at least a portion of the subterranean formation, a wellbore, a subterranean formation, a vessel, and/or a conduit (and/or into a fluid within any of the foregoing) using any method or equipment known in the art. For example, the hydrate inhibitor compounds of the present disclosure may be applied to a subterranean formation and/or wellbore using batch treatments, squeeze treatments, continuous treatments, and/or any combination thereof. In certain embodiments, a batch treatment may be performed in a subterranean formation by stopping production from the well and pumping the dissolved hydrate inhibitors into a wellbore, which may be performed at one or more points in time during the life of a well. In other embodiments, a squeeze treatment may be performed by dissolving a hydrate inhibitor compound of the present disclosure in a suitable solvent at a suitable concentration and squeezing that solvent carrying the hydrate inhibitor downhole into the formation, allowing production out of the formation to bring the hydrate inhibitor to its desired location. In other embodiments, a hydrate inhibitor compound of the present disclosure may be injected into a portion of a subterranean formation using an annular space or capillary injection system to continuously introduce the hydrate inhibitor compound into the formation. In certain embodiments, a composition (such as a treatment fluid) including a hydrate inhibitor compound of the present disclosure may be circulated in the wellbore using the same types of pumping systems and equipment at the surface that are used to introduce treatment fluids or additives into a wellbore penetrating at least a portion of the subterranean formation.

In certain embodiments, the methods of the present disclosure include applying the hydrate inhibitor compound to a fluid. In some embodiments, the method of applying the hydrate inhibitor compound to prevent hydrate plugging includes introducing the hydrate inhibitor compound into an umbilical line or a capillary line in which a fluid is located.

In certain embodiments, the fluids or additives may be formed at a well site where the operation or treatment is conducted, either by batch mixing or continuous ("on-the-fly") mixing. The term "on-the-fly" is used herein to include methods of combining two or more components wherein a flowing stream of one element is continuously introduced into a flowing stream of at least one other component so that the streams are combined and mixed while continuing to flow as a single stream as part of the on-going treatment. Such mixing can also be described as "real-time" mixing. In other embodiments, the treatment fluids of the present disclosure may be prepared, either in whole or in part, at an offsite location and transported to the site where the treatment or operation is conducted. In introducing a composition of the present disclosure into a vessel, conduit (e.g., an umbilical, capillary, or tubing), wellbore, and/or portion of a subterranean formation, components of the composition may be mixed together prior to introduction into a vessel, conduit, wellbore, and/or formation together, or one or more components may be introduced into the vessel, conduit, wellbore, and/or formation at the surface separately from other components such that the components mix or intermingle in a portion of the vessel, conduit, wellbore, and/or formation to form a composition. In either such case, the composition is deemed to be introduced into at least a portion of the vessel, conduit, wellbore, and/or subterranean formation for purposes of the present disclosure.

Figure 3:
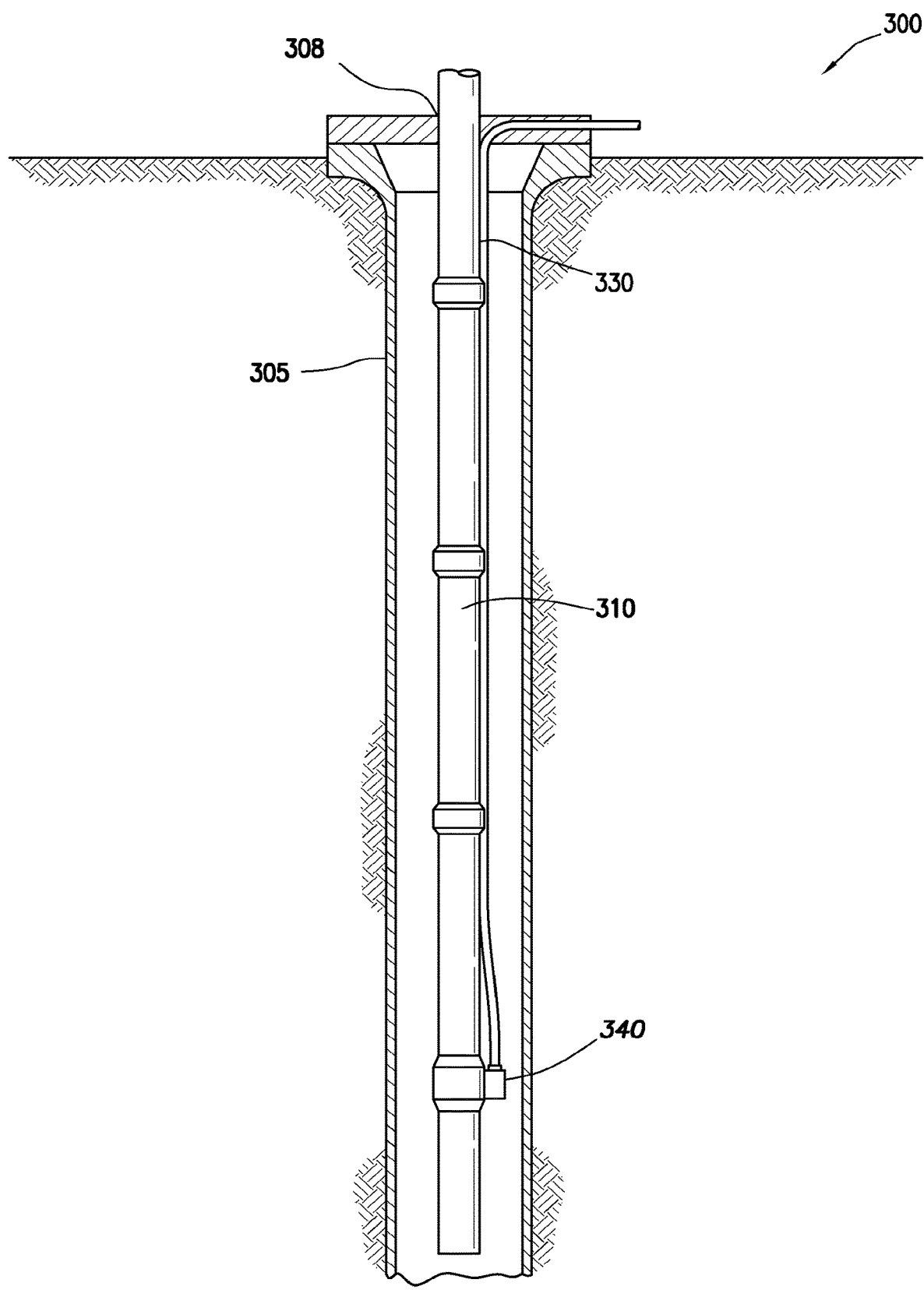
FIG. 3 is a diagram illustrating an injection system used in accordance with certain embodiments of the present disclosure.

For example, a hydrate inhibitor compound of the present disclosure may be introduced into a wellbore and/or tubing using a capillary injection system as shown in FIG. 3. Referring now to FIG. 3, wellbore 305 has been drilled to penetrate a portion of a subterranean formation 300. A tubing 310 (e.g., production tubing) has been placed in the wellbore 305. A capillary injection tube 330 is disposed in the annular space between the outer surface of tubing 310 and the inner wall of wellbore 305. The capillary injection tube 330 is connected to a side-pocket mandrel 340 at a lower section of the tubing 310. A hydrate inhibitor compound of the present disclosure may be injected into capillary injection tube 330 at the wellhead 308 at the surface such that it mixes with production fluid at or near the side-pocket mandrel 340. As the production fluid flows through the tubing 310, the hydrate inhibitor compound may prevent, inhibit, retard, reduce, control, and/or delay the formation of one or more hydrates within the tubing 310. Other capillary injection systems and side pocket mandrel devices (e.g., those used in gas lift production) may be used in a similar manner to the system shown in FIG. 3.

In certain embodiments, a hydrate inhibitor compound of the present disclosure may be added to a conduit such as a pipeline where one or more fluids enter the conduit and/or at one or more other locations along the length of the conduit. In such embodiments, the hydrate inhibitor compound may be added in batches or injected substantially continuously while the pipeline is being used, for example, to maintain the concentration of the hydrate inhibitor compound of the present disclosure in the fluid at a certain amount (e.g., one or more of the concentrations referenced above).

Once introduced into a fluid, subterranean formation, wellbore, pipeline, vessel, or other location, the hydrate inhibitor compound may inhibit, retard, reduce, control, and/or delay the formation of one or more hydrates or the agglomeration of hydrate crystals within the fluid, subterranean formation, wellbore, pipeline, vessel, or other location.

To facilitate a better understanding of the present disclosure, the following examples of certain aspects of certain embodiments are given. The following examples are not the only examples that could be given according to the present disclosure and are not intended to limit the scope of the disclosure or claims.

EXAMPLE

Rocking cell tests were carried out on several samples including different hydrate inhibitor compounds having structures according to some embodiments of the present disclosure. Rocking cell tests involved the injection of oil, water, a hydrate inhibitor compound, and gas into a cell at representative conditions. Gas was injected into the cell to achieve a desired working pressure during the experiment. Each cell was of a fixed volume and contained constant mass during the experiment; that is, oil, water, a hydrate inhibitor compound, and gas were injected at the beginning of the experiment, but thereafter the cell was closed to mass transfer in or out of the cell. Each cell also included a magnetic ball in the space where fluids are injected. The ball aided in agitation of the fluids during rocking. In addition, magnetic sensors on both ends of the cell detected whether the magnetic ball's movements through the fluids were hindered during rocking, wherein such hindrance could indicate the presence of hydrates. The cell also permitted visual observation of its contents during the experiment.

Initially, amounts of Mission Condensate oil, 6% NaCl, and a hydrate inhibitor compound were injected into the cell so as to achieve a water cut of 55% (i.e., fraction of aqueous phase by volume in the total fluid) and a hydrate inhibitor compound dosage of 0.25 to 5% by volume of the water phase (i.e., volume % of hydrate inhibitor compound on water cut basis). After injection of oil, brine, and hydrate inhibitor compound, gas was injected to reach a desired pressure (e.g., working pressure of a conduit of interest for evaluation of the hydrate inhibitor compound, in this case around 2,800 psi).

Following injection of the gas, the cell was closed and rocked for approximately 2 hours to emulsify the fluids therein. The temperature was then ramped down from about 20° C. to about 4° C. over a period of about 1 hour, and rocking was continued for around 16 hours after the temperature reached about 4° C. The rocking was then stopped for a period of time while the cell is horizontal (e.g., to simulate a system shut-in). This "shut-in" period lasts for at least 6 hours, varying only so that the restart of rocking could be visually observed.

Visual inspection of the contents of the cell was made throughout the tests for visual rating of the performance of the hydrate inhibitor compound as a hydrate inhibitor. Samples were prepared of compositions including hydrate inhibitor compounds with structures according to some embodiments of the present disclosure. The samples prepared included hydrate inhibitor compounds having the following structure:

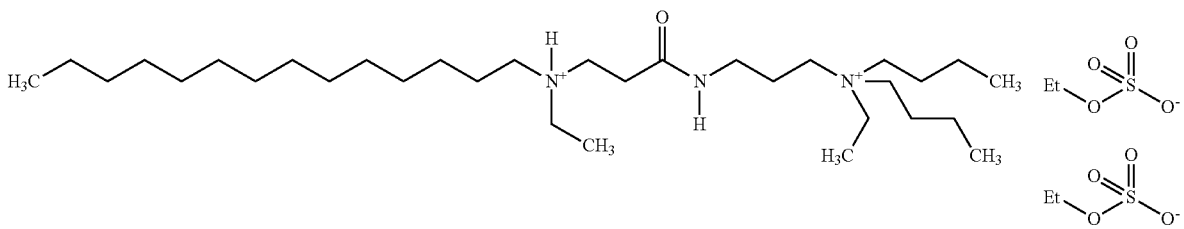 [SMILES: CCCCCCCCCCCCCC[NH+](CC)CCC(=O)NCCC[N+](CC)(CCCC)CCCC ; CCOS(=O)(=O)[O-] ; CCOS(=O)(=O)[O-]]

The samples having the above structure passed the rocking cell test in the fluid with a water cut of 55%. These results of the rocking cell tests indicated that the compositions and methods of the present disclosure may facilitate, among other benefits, the inhibition, retardation, reduction, control, and/or delay of agglomeration of hydrates and/or hydrate-forming compounds in fluids having a water cuts as high as 55%.

An embodiment of the present disclosure is a method including: introducing a hydrate inhibitor composition into a fluid, wherein the hydrate inhibitor composition includes at least one compound having the structural formula:

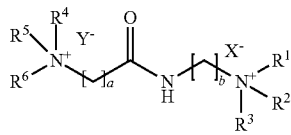

wherein each of $R^1$, $R^2$, and $R^3$ is independently a $C_1$ to $C_6$ hydrocarbon chain, wherein $R^4$ is selected from the group consisting of hydrogen and any $C_1$ to $C_{50}$ hydrocarbon chain, wherein each of $R^5$ and $R^6$ is independently selected from the group consisting of hydrogen and a $C_1$ to $C_{50}$ hydrocarbon chain, wherein $X^-$ and $Y^-$ are counter anions, and wherein each of a and b is independently an integer from 1 to 10.

In one or more embodiments described above, $X^-$ and $Y^-$ are selected from the group consisting of: a carboxylate, a halide, a sulfate, an organic sulfonate, a phosphate, a phosphonate, a hydroxide, and any combination thereof. In one or more embodiments described above, the fluid includes at least one component selected from the group consisting of: water, a gas, a liquid hydrocarbon, and any combination thereof. In one or more embodiments described above, the hydrate inhibitor composition is introduced into the fluid through a conduit or an injection point in fluid communication with a wellbore in which the fluid resides. In one or more embodiments described above, the hydrate inhibitor composition is introduced into a wellbore penetrating at least a portion of a subterranean formation through which the fluid is flowing. In one or more embodiments described above, the fluid includes water and has a water cut of up to 80%. In one or more embodiments described above, the hydrate inhibitor composition is introduced into the fluid through an umbilical or a capillary line. In one or more embodiments described above, the fluid includes water and the hydrate inhibitor composition is introduced into the fluid in an amount such that the compound is present in the fluid in an amount from about 0.1% to about 10% by volume based on the water cut of the fluid. In one or more embodiments described above, each of $R^4$ and $R^5$ is a $C_1$ to $C_{50}$ hydrocarbon chain resulting from a reaction between an acrylate or a methacrylate and an amine, the amine being selected from the group consisting of: a synthetic primary or secondary amine selected from the group consisting of: butylamine, pentylamine, hexylamine, octylamine, dodecylamine, N-methyldodecylamine, N-methyloctylamine, didodecylamine, and any combination thereof; a primary or secondary fatty amine derived from one or more fatty acids selected from the group consisting of: corn oil, canola oil, coconut oil, safflower oil, sesame oil, palm oil, cottonseed oil, soybean oil, olive oil, sunflower oil, hemp oil, wheat germ oil, tall oil, palm kernel oil, vegetable oil, tallow oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof; and any combination thereof. In one or more embodiments described above, the at least one compound is a reaction product of a reaction between (i) an alkylating agent and (ii) a second intermediate resulting from a reaction between a dialkylaminoalkylamine and a first intermediate, the first intermediate resulting from a reaction between an acrylate or a methacrylate and an amine. In one or more embodiments described above, the fluid resides in a wellbore penetrating at least a portion of a subterranean formation.

In another embodiment, the present disclosure provides a method including introducing a hydrate inhibitor composition into a conduit through which a fluid is flowing, wherein the hydrate inhibitor composition includes at least one compound having the structural formula:

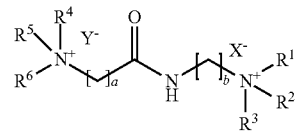

wherein each of $R^1$, $R^2$, and $R^3$ is independently a $C_1$ to $C_6$ hydrocarbon chain, wherein $R^4$ is selected from the group consisting of hydrogen and any $C_1$ to $C_{50}$ hydrocarbon chain, wherein each of $R^5$ and $R^6$ is independently selected from the group consisting of hydrogen and a $C_1$ to $C_{50}$ hydrocarbon chain, wherein $X^-$ and $Y^-$ are counter anions, and wherein each of a and b is independently an integer from 1 to 10.

In one or more embodiments described above, $X^-$ and $Y^-$ are selected from the group consisting of: a carboxylate, a halide, a sulfate, an organic sulfonate, a phosphate, a phosphonate, a hydroxide, and any combination thereof. In one or more embodiments described above, the fluid includes at least one component selected from the group consisting of: water, a gas, a liquid hydrocarbon, and any combination thereof. In one or more embodiments described above, the fluid includes water and has a water cut of up 80%. In one or more embodiments described above, each of $R^4$ and $R^5$ is a $C_1$ to $C_{50}$ hydrocarbon chain resulting from a reaction between an acrylate or a methacrylate and an amine, the amine being selected from the group consisting of: a synthetic primary or secondary amine selected from the group consisting of butylamine, pentylamine, hexylamine, octylamine, dodecylamine, N-methyldodecylamine, N-methyloctylamine, didodecylamine, and any combination thereof; a primary or secondary fatty amine derived from one or more fatty acids selected from the group consisting of: corn oil, canola oil, coconut oil, safflower oil, sesame oil, palm oil, cottonseed oil, soybean oil, olive oil, sunflower oil, hemp oil, wheat germ oil, tall oil, palm kernel oil, vegetable oil, tallow oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof; and any combination thereof.

In another embodiment, the present disclosure provides a composition including compound having the structural formula:

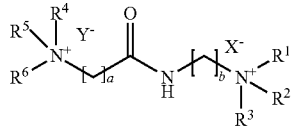

wherein each of $R^1$, $R^2$, and $R^3$ is independently a $C_1$ to $C_6$ hydrocarbon chain, wherein $R^4$ is selected from the group consisting of hydrogen and any $C_1$ to $C_{50}$ hydrocarbon chain, wherein each of $R^5$ and $R^6$ is independently selected from the group consisting of hydrogen and a $C_1$ to $C_{50}$ hydrocarbon chain, herein $X^-$ and $Y^-$ are counter anions, and wherein each of a and b is independently an integer from 1 to 10.

In one or more embodiments described above, $X^-$ and $Y^-$ are selected from the group consisting of: a carboxylate, a halide, a sulfate, an organic sulfonate, a phosphate, a phosphonate, a hydroxide, and any combination thereof. In one or more embodiments described above, each of $R^4$ and $R^5$ is a $C_1$ to $C_{50}$ hydrocarbon chain resulting from a reaction between an acrylate or a methacrylate and an amine, the amine being selected from the group consisting of: a synthetic primary or secondary amine selected from the group consisting of: butylamine, pentylamine, hexylamine, octylamine, dodecylamine, N-methyldodecylamine, N-methyloctylamine, didodecylamine, and any combination thereof; a primary or secondary fatty amine derived from one or more fatty acids selected from the group consisting of: corn oil, canola oil, coconut oil, safflower oil, sesame oil, palm oil, cottonseed oil, soybean oil, olive oil, sunflower oil, hemp oil, wheat germ oil, tall oil, palm kernel oil, vegetable oil, tallow oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof; and any combination thereof. In one or more embodiments described above, the composition further includes a solvent selected from the group consisting of: an alcohol, methanol, ethanol, isopropyl alcohol, glycol, glycol ethers, an organic solvent, toluene, xylene, monobutyl ether, hexane, cyclohexane, and any combination thereof.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:
1. A method comprising:
introducing a hydrate inhibitor composition into a fluid, wherein the hydrate inhibitor composition comprises at least one compound of the structural formula:

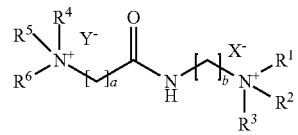

wherein each of $R^1$, $R^2$, and $R^3$ is independently a $C_1$ to $C_6$ hydrocarbon chain,
wherein $R^4$ is selected from the group consisting of hydrogen and any $C_1$ to $C_{50}$ hydrocarbon chain,
wherein each of $R^5$ and $R^6$ is independently selected from the group consisting of hydrogen and a $C_1$ to $C_{50}$ hydrocarbon chain,
wherein $X^-$ and $Y^-$ are counter anions, and
wherein each of a and b is independently an integer from 1 to 10.

2. The method of claim 1 wherein $X^-$ and $Y^-$ are selected from the group consisting of: a carboxylate, a halide, a sulfate, an organic sulfonate, a phosphate, a phosphonate, a hydroxide, and any combination thereof.

3. The method of claim 1 wherein the fluid comprises at least one component selected from the group consisting of: water, a gas, a liquid hydrocarbon, and any combination thereof.

4. The method of claim 1 wherein the hydrate inhibitor composition is introduced into the fluid through a conduit or an injection point in fluid communication with a wellbore in which the fluid resides.

5. The method of claim 1 wherein the hydrate inhibitor composition is introduced into a wellbore penetrating at least a portion of a subterranean formation through which the fluid is flowing.

6. The method of claim 1 wherein the fluid comprises water and has a water cut of up to 80%.

7. The method of claim 1 wherein the hydrate inhibitor composition is introduced into the fluid through an umbilical or a capillary line.

8. The method of claim 1 wherein the fluid comprises water and the hydrate inhibitor composition is introduced into the fluid in an amount such that the compound is present in the fluid in an amount from about 0.1% to about 10% by volume based on the water cut of the fluid.

9. The method of claim 1 wherein each of $R^4$ and $R^5$ is a $C_1$ to $C_{50}$ hydrocarbon chain resulting from a reaction between an acrylate or a methacrylate and an amine, the amine being selected from the group consisting of:
a synthetic primary or secondary amine selected from the group consisting of: butylamine, pentylamine, hexylamine, octylamine, dodecylamine, N-methyldodecylamine, N-methyloctylamine, didodecylamine, and any combination thereof;
a primary or secondary fatty amine derived from one or more fatty acids selected from the group consisting of: corn oil, canola oil, coconut oil, safflower oil, sesame oil, palm oil, cottonseed oil, soybean oil, olive oil, sunflower oil, hemp oil, wheat germ oil, tall oil, palm kernel oil, vegetable oil, tallow oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof; and
any combination thereof.

10. The method of claim 1 wherein the at least one compound is a reaction product of a reaction between (i) an alkylating agent and (ii) a second intermediate resulting from a reaction between a dialkylaminoalkylamine and a first intermediate, the first intermediate resulting from a reaction between an acrylate or a methacrylate and an amine.

11. The method of claim 1, wherein the fluid resides in a wellbore penetrating at least a portion of a subterranean formation.

12. A method comprising:
introducing a hydrate inhibitor composition into a conduit through which a fluid is flowing, wherein the hydrate inhibitor composition comprises at least one compound of the structural formula:

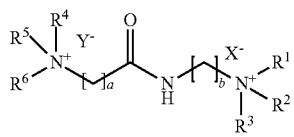

wherein each of $R^1$, $R^2$, and $R^3$ is independently a $C_1$ to $C_6$ hydrocarbon chain,
wherein $R^4$ is selected from the group consisting of hydrogen and any $C_1$ to $C_{50}$ hydrocarbon chain,
wherein each of $R^5$ and $R^6$ is independently selected from the group consisting of hydrogen and a $C_1$ to $C_{50}$ hydrocarbon chain,
wherein $X^-$ and $Y^-$ are counter anions, and
wherein each of a and b is independently an integer from 1 to 10.

13. The method of claim 12 wherein $X^-$ and $Y^-$ are selected from the group consisting of: a carboxylate, a halide, a sulfate, an organic sulfonate, a phosphate, a phosphonate, a hydroxide, and any combination thereof.

14. The method of claim 12 wherein the fluid comprises at least one component selected from the group consisting of: water, a gas, a liquid hydrocarbon, and any combination thereof.

15. The method of claim 12 wherein the fluid comprises water and has a water cut of up 80%.

16. The method of claim 12 wherein each of $R^4$ and $R^5$ is a $C_1$ to $C_{50}$ hydrocarbon chain resulting from a reaction between an acrylate or a methacrylate and an amine, the amine being selected from the group consisting of:
a synthetic primary or secondary amine selected from the group consisting of: butylamine, pentylamine, hexylamine, octylamine, dodecylamine, N-methyldodecylamine, N-methyloctylamine, didodecylamine, and any combination thereof;
a primary or secondary fatty amine derived from one or more fatty acids selected from the group consisting of: corn oil, canola oil, coconut oil, safflower oil, sesame oil, palm oil, cottonseed oil, soybean oil, olive oil, sunflower oil, hemp oil, wheat germ oil, palm kernel oil, vegetable oil, tall oil, tallow oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof; and
any combination thereof.

17. A method comprising:
introducing a hydrate inhibitor composition into a conduit through which a fluid is flowing, wherein the hydrate inhibitor composition comprises at least one compound of the structural formula:

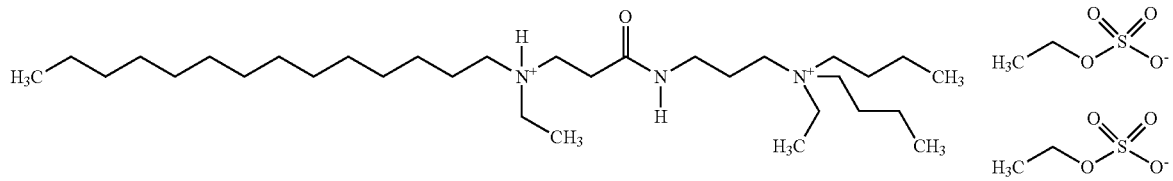

18. The method of claim 17 wherein the fluid comprises at least one component selected from the group consisting of: water, a gas, a liquid hydrocarbon, and any combination thereof.

19. The method of claim 17 wherein the fluid comprises water and has a water cut of up to 80%.

20. The method of claim 17 wherein the fluid comprises water and the hydrate inhibitor composition is introduced into the fluid in an amount such that the compound is present in the fluid in an amount from about 0.1% to about 10% by volume based on the water cut of the fluid.

* * * * *